United States Patent [19]
Eshel et al.

[11] Patent Number: 4,823,812
[45] Date of Patent: Apr. 25, 1989

[54] APPLICATOR FOR INSERTION INTO A BODY OPENING FOR MEDICAL PURPOSES

[75] Inventors: Uzi Eshel, Herzlia; Avigdor Lev, Petach Tikva, both of Israel

[73] Assignee: Biodan Medical Systems Ltd., Kiryat Weizmann, Israel

[21] Appl. No.: 46,195

[22] Filed: May 5, 1987

[30] Foreign Application Priority Data

May 12, 1986 [IL] Israel .................................. 78755

[51] Int. Cl.$^4$ ............................................. A61N 5/02
[52] U.S. Cl. ...................................... 128/804; 128/401; 128/784; 604/96
[58] Field of Search ............... 128/642, 736, 399, 401, 128/804, 344, 303.1, 6, 784; 604/96, 101, 103

[56] References Cited

U.S. PATENT DOCUMENTS

| 3,417,753 | 12/1968 | Mattler | 604/103 X |
| 3,435,826 | 4/1969 | Fogarty | 128/344 X |
| 4,040,413 | 8/1977 | Ohshiro | 128/6 |
| 4,204,549 | 5/1980 | Paglione | 128/804 X |
| 4,295,464 | 10/1981 | Shihata | 128/344 X |
| 4,375,220 | 3/1983 | Matvias | 128/401 X |
| 4,601,296 | 7/1986 | Yeroshelmi | 128/804 |
| 4,612,940 | 9/1986 | Kasevich et al. | 128/804 |
| 4,627,436 | 12/1986 | Leckrome | 128/303.1 |

FOREIGN PATENT DOCUMENTS 0105677 4/1984 European Pat. Off. ............ 128/804

OTHER PUBLICATIONS

Mendecki et al., "Microwave Applicators ... Prostate", Int. J Rad. Onc Biol Phy, vol. 6, No. 11, Nov. 1980, pp. 1583–1588.

Primary Examiner—Lee S. Cohen
Attorney, Agent, or Firm—Benjamin J. Barish

[57] ABSTRACT

An applicator for insertion into a body opening for medical treatment or for diagnostic purposes comprises an elongated jacket for insertion into the body opening, a disposable sleeve received on the jacket, and a balloon integrally formed on the disposable sleeve at one side of the jacket. The balloon is inflatable by a fluid to press the opposite side of the jacket and sleeve laterally against the tissue of the body opening, thereby to fix the position of the jacket within the body opening and to conform the pressed body tissue to the shape of the opposite side of the jacket. The applicator further includes a microwave antenna disposed within the jacket, the jacket further including cooling ducts adjacent its outer surface for circulating a cooling fluid therethrough in order to prevent undue heating of the body tissue in direct contact with the jacket.

10 Claims, 3 Drawing Sheets

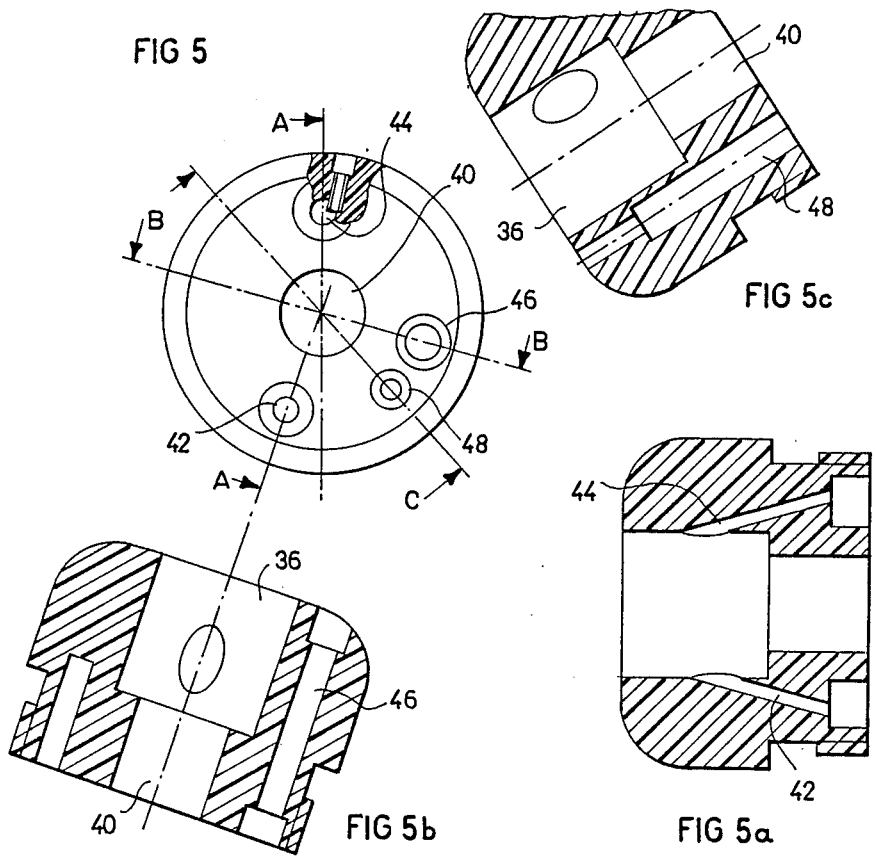
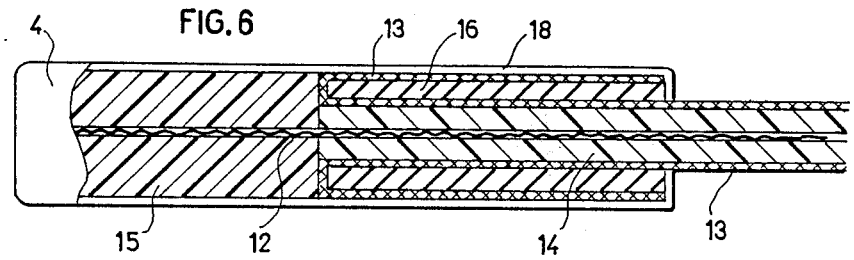

APPLICATOR FOR INSERTION INTO A BODY OPENING FOR MEDICAL PURPOSES

BACKGROUND OF THE INVENTION

The present invention relates to an applicator adapted to be inserted into a body opening for various medical purposes, e.g. for medical treatment or medical diagnosis. The invention is particularly useful as a heating applicator for insertion through the anus into the rectum of a patient for use in hyperthermia treatments, and is therefore described below with respect to this application.

The applicator of the present invention is particularly useful with the catheter and probe described in our Companion Application No. 07/046,193 filed the same date as this Application.

Hyperthermia is a recognized technique for rendering certain therapeutic treatments to a patient by the application of heat to the portion of the patient's body to be treated. A large number of applicators have been developed for treating cancer, or for other therapeutic purposes such as the treatment of hemorrhoids, as described for example in U.S. Pat. Nos. 4,375,220, 4,312,364, 4,311,154, 4,227,535, 4,186,729, 4,154,246, 4,140,130, 4,016,886, 2,043,083, 2,032,859 and 1,433,286.

An object of the present invention is to provide an applicator for insertion into a body opening for purposes of performing a medical treatment or a medical diagnosis. Another object of the invention is to provide an applicator particularly useful for a hyperthermia treatment. Further objects of the invention are to provide a disposable sleeve, and also a microwave antenna, particularly useful with the above-mentioned applicator.

BRIEF SUMMARY OF THE INVENTION

According to the present invention, there is provided an applicator for insertion into a body opening for medical treatment or for diagnostic purposes, characterized in that the applicator includes: an elongated jacket having a proximal open end and a distal closed end for insertion into the body opening; a disposable sleeve of elastomeric material also having a proximal open end and a distal closed end received on said jacket; and a balloon of elastomeric material integrally formed with and joined to said disposable sleeve at one thereof, said balloon occupying only the distal end of the disposable sleeve and being inflatable by a fluid to press the opposite side of the jacket and sleeve laterally against the tissue of the body opening, thereby to fix the position of the jacket within the body opening and to conform the pressed body tissue to the shape of said opposite side of the jacket According to another important feature of the present invention, the inflatable balloon is of generally conical configuration when inflated, having a narrow tip joined to the sleeve and a wide base engageable with the body tissue.

The invention is particularly useful for rendering hyperthermia treatments. For such an application, the applicator further includes a microwave antenna disposed within the jacket, the jacket further including cooling ducts adjacent its outer surface for circulating a cooling fluid therethrough in order to prevent undue heating of the body tissue in direct contact therewith. The balloon, when inflated, thereby also effects efficient cooling of the body tissue in contact with the opposite side of the jacket. The applicator may thus be used for heating tissue directly in contact with the outer face of the applicator, in which case a cooling fluid would not be circulated through the cooling ducts; alternatively, the applicator may be used for heating more remotely-located tissue, in which case a cooling fluid would be circulated through the cooling ducts in order to prevent undue heating of the tissue in direct contact with the applicator.

According to a further feature the present invention, also provides a microwave antenna for use in an applicator to be inserted into a body opening for medical treatment, characterized in the microwave antenna includes an inner electrical conductor, a layer of dielectric thereover serving as dielectric loading, and an outer electrical conductor in the form of a braid; the outer electrical braid being folded back over itself and dielectrically separated from the underlying electrical braid by another dielectric layer, thereby forming a dielectric loaded antenna in which the folded back portion of the electrical braid serves as an RF choke suppressing electromagnetic interference.

In the described embodiment, the jacket further includes a reflector at one side for reflecting the microwave energy produced by the antenna through the opposite side, and for concentrating the energy to a selected region of the body tissue at the opposite side.

Further features and advantages of the invention will be apparent from the description below.

BRIEF DESCRIPTION OF THE DRAWINGS

The invention is herein described, by way of example only, with reference to the accompanying drawings, wherein:

FIG. 5 is an end view, partly in section, of the end fitting in the applicator of FIG. 1;

FIGS. 5a, 5b and 5c are sectional views along lines a—a, b—b, c—c, respectively, of FIG. 5;

and FIG. 6 is a sectional view of the microwave antenna used as the heating element in the applicator of FIG. 1.

DESCRIPTION OF A PREFERRED EMBODIMENT

Figure 1:
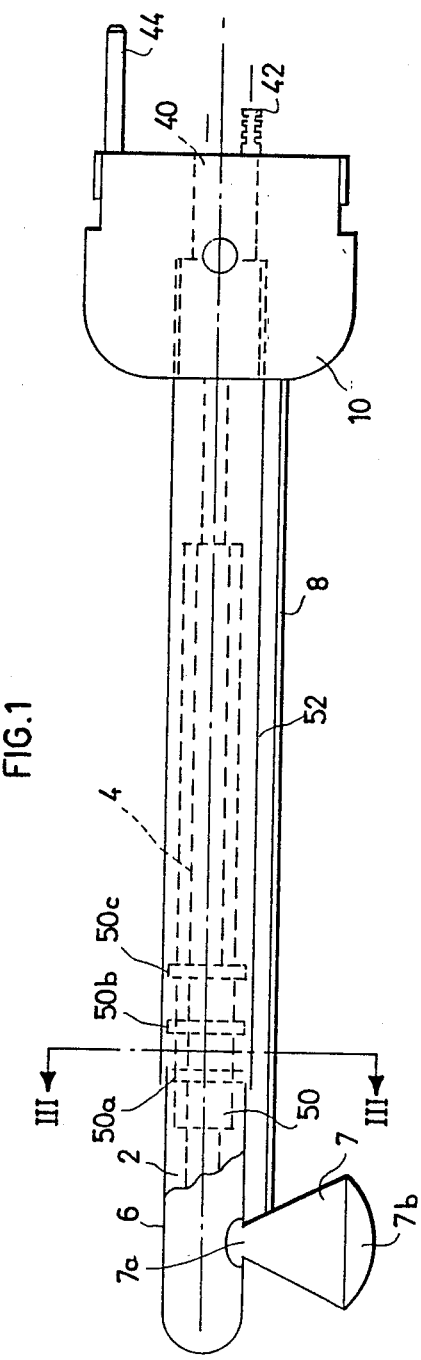
FIG. 1 is a side elevational view illustrating one form of heating applicator constructed in accordance with the present invention, the sleeve and balloon carried by the applicator being shown in its inflated condition.

The applicator illustrated in the drawings comprises an elongated jacket, generally designated 2, for insertion into a body cavity at the location of the tissue to be heated. The applicator illustrated in FIG. 1 is particularly designed for insertion via the body anus into the rectum for treating this region of the body, although it will be appreciated that the invention could be applied to other body cavities and used for other therapeutic treatments or for diagnostic purposes.

The illustrated applicator includes a heating element in the form of a microwave antenna, indicated by broken lines 4 in FIG. 1 but more particularly illustrated in FIG. 6, generating RF electromagnetic radiation for heating the body tissue. The applicator further includes a disposable sleeve 6, carried by the jacket 2 and integrably formed with a balloon 7 projecting laterally at the distal end of the sleeve. Balloon 7 is inflatable by air or water applied via a tubelet 8 extending through an end fitting 10 externally of the sleeve. The balloon 7 is of generally conical configuration when inflated, having a narrow tip 7a joined to the sleeve 6, and a wide base 7b at its opposite end engageable with the body tissue at one side of the body opening when the balloon is inflated while the applicator is within the body opening.

Antenna 4 is more particularly illustrated in FIG. 6. It is constructed of a coaxial cable including an inner electrical conductor 12 and an outer electrical conductor braid 13 separated from the inner conductor by a dielectric layer 14. The dielectric layer 14 is removed from the end of the coaxial cable to bare the inner conductor 12, and the inner conductor is then covered by a dielectric layer 15, e.g. glass or ceramic having a dielectric constant of at least 2. The outer conductor braid at the end of the cable is folded back over itself and is separated from the underlying braid by a dielectric layer 16. The outer face of the antenna is then covered by a protective coating 18, as by dipping in a bath of insulating material.

Figure 2:
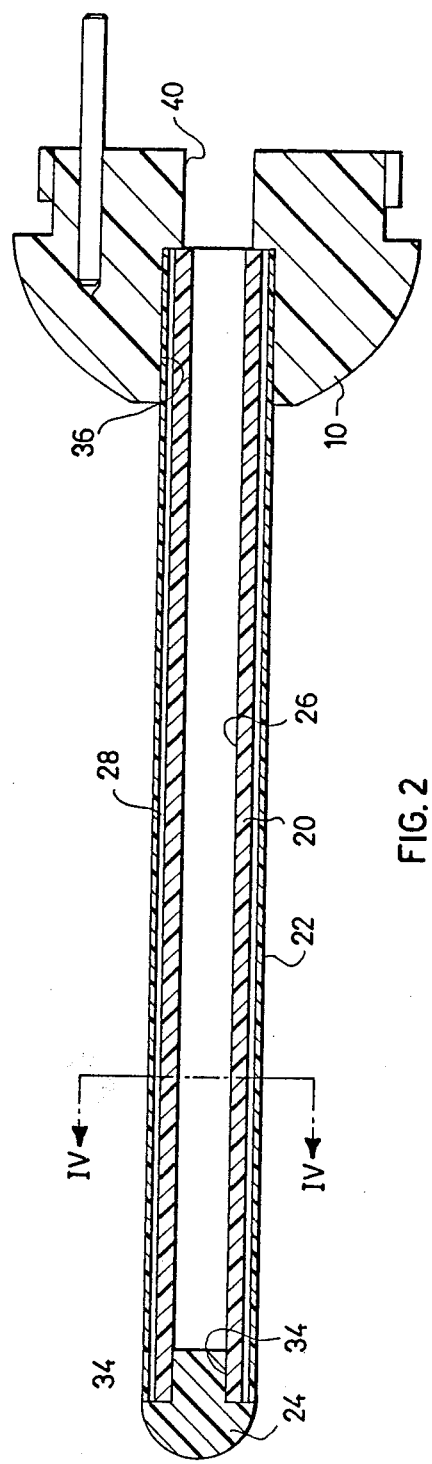
FIG. 2 is a longitudinal sectional view of the applicator of FIG. 1 with the heating element and balloon-sleeve removed.
Figure 3:
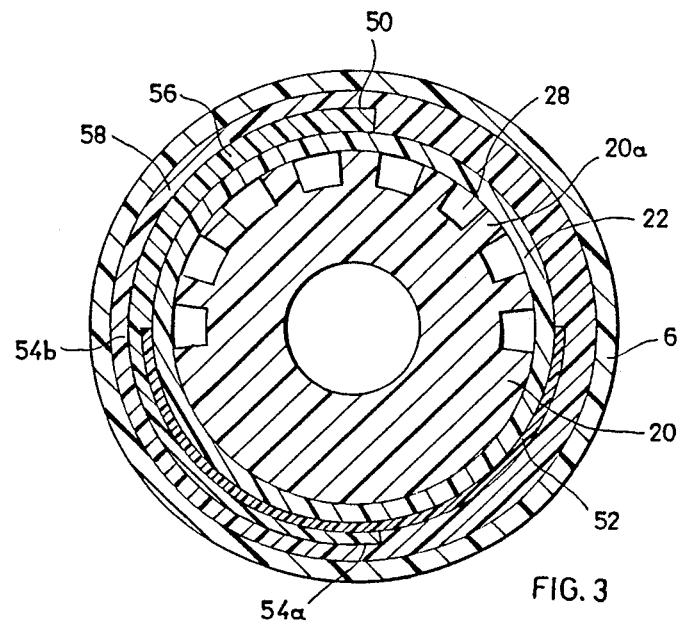
FIG. 3 is a transverse sectional view along lines III—III of FIG. 1.

As shown more particularly in FIGS. 2 and 3, jacket 2 includes an inner, relatively thick core 20, an outer thin sleeve 22, and a solid tip 24 at the distal end of the applicator. Inner core 20 is formed with an axially-extending bore 26 for receiving the microwave antenna 4, and its outer face is formed with a plurality of axially-extending ribs 20a to define a plurality of recessed channels 28, as more particularly illustrated in FIGS. 3 and 4. Channels 28 form, with the outer sleeve 22, a plurality of cooling ducts for circulating a cooling fluid, such as water.

Figure 4:
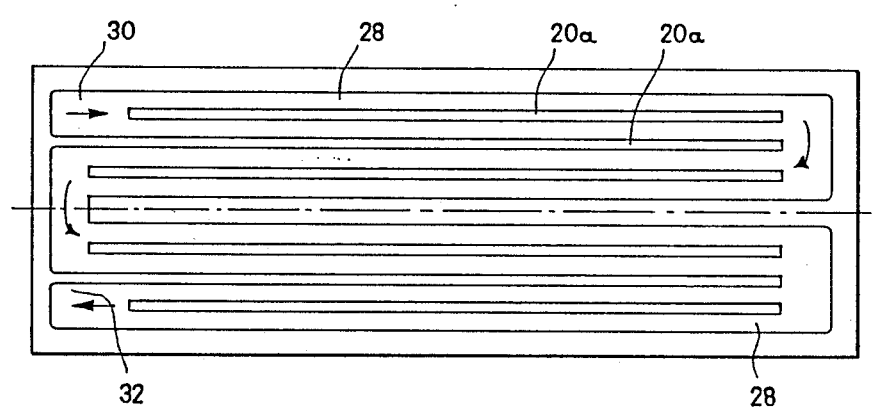
FIG. 4 is a diagrammatic view illustrating the formation of the channels in the outer face of the inner sleeve, which channels cooperate with the outer sleeve of the jacket to define the cooling ducts.

As shown in FIG. 4, the cooling ducts defined by recessed channels 28 extend the complete length of the jacket in a sinuous manner from the cooling fluid inlet 30 at the proximal end of the applicator (left end in FIG. 4, but right end in FIGS. 1 and 2) back and forth with respect to the opposite, distal end of the applicator, the water exiting via the water outlet 32 at the proximal end of the applicator.

The solid tip 24 at the distal end of the applicator is formed with an annular recess 34 for receiving the distal ends of the inner core 20 and the outer sleeve 22. The proximal ends of these sleeves are received within a cylindrical recess 36 formed centrally of the end fitting 10.

End fitting 10 is further formed with a central bore 40 for passing the microwave heating antenna 4 therethrough into the bore 26 of the inner core 20. Fitting 10 is further formed with a pair of lateral bores 42, 44 (FIGS. 5, 5a) communicating with the cooling ducts 28 for circulating the cooling fluid, (e.g., water) therethrough. Bore 42 is the inlet for the cooling water, and bore 44 is the outlet.

End fitting 10 is formed with a further bore 46 (FIGS. 5, 5b) serving as the inlet for admitting air or water to inflate balloon 7 via tubelet 8 received within bore 46 and connected to the balloon. End fitting 10 includes a still further bore 48 (FIGS. 5, 5c) for receiving the electrical leads of three thermocouples 50a, 50b, 50c (FIG. 1) which measure the temperature within the body opening into which the applicator has been inserted.

The inner core 20 is formed, for approximately one-half its circumference, with the ribs 20a defining the cooling ducts 28; for the other half of its circumference, the outer face of sleeve 22 is lined with a copper reflector layer 52, as shown in FIG. 3, extending substantially along the complete length of the sleeve, this being at the side of the jacket carrying the inflatable balloon 7. Copper layer 52 reflects the electromagnetic radiation generated by the microwave antenna 4 in the direction away from balloon 7 so that the generated heat is concentrated in the body tissue at the side of the body opening opposite to the balloon.

Thermocouples 50a, 50b, 50c (FIG. 1) are disposed substantially at the outer surface of jacket 2 adjacent to its distal end, and are spaced from each other a slight distance longitudinally of the jacket, as shown in FIG. 1, in order to measure the temperature at these three selected regions of the body cavity in which the applicator is inserted. The electrical conductors to these thermocouples pass axially along the side of the jacket occupied by reflector 52, on the outer face of the reflector as shown at 54a in FIG. 3, to the axial location of the respective thermocouple, and then pass circumferentially along the outer face of the reflector to their respective thermocouple, as shown at 54b in FIG. 3. Reflector 52 thus substantially shields the electrical conductors from the electromagnetic field produced by the antenna.

An insulating layer 56 is applied to insulate electrical conductors 54a, 54b from the reflector 52, and also to insulate the thermocouples 50a-50c from the cooling effect produced by the cooling fluid circulated through the cooling ducts 28. An outer thin protective layer, such as a dipped coating, is applied to the outer face of jacket 2 covering the thermocouples 50a-50c and their electrical conductors 54a, 54b.

The disposable sleeve 6, including the balloon 7 and tubelet 8, is supplied separately and may be applied to the outer face of the applicator 2 just before it is intended to be used. Sleeve 6 is preferably formed integrally with balloon 7 from an elastomer, e.g., rubber latex. For sanitary purposes, the sleeve is disposable for one-time use.

The manner of using the heating applicator illustrated in the drawings will be apparent from the above description. Thus, after a sleeve 6, with its integrally formed balloon 7 has been applied to the applicator, the applicator is inserted into the body opening, for example into the rectum via the anus, while balloon 7 is deflated. When the distal end (left end) of the applicator is in proper position within the body opening, balloon 7 is inflated by pressurized air or water applied via bore 46 in end fitting 10, and tubelet 8. The inflation of the balloon causes it to firmly press the opposite side of the applicator against the body tissue in the opening. Electrical current is then applied to the microwave antenna 4 in order to generate a microwave field for heating the body tissue opposite to balloon 7, this energy being concentrated by reflector 52. During the heating of the body tissue, water may be circulated via the cooling ducts 28 to cool the outer surface of the jacket, while the temperature within the body opening is measured by thermocouples 50a, 50b, 50c.

It will thus be seen that the inflation of balloon 7 at the distal end of the applicator displaces the applicator laterally within the body opening, thereby firmly pressing the side thereof through which the microwave radiation is transmitted (namely the side opposite to that occupied by balloon 7 and reflector 52) firmly against the body tissue. This fixes the position of the jacket, and thereby of the microwave antenna 4, within the body opening, and also conforms the pressed body tissues to the shape of the jacket at the opposite side of reflector 52.

The inflation of balloon 7 also enhances the cooling effect produced by the water circulated through the cooling ducts 28, thereby efficiently cooling the body tissue in direct contact with the applicator. This permits the application of relatively large amounts of heat to relatively remote tissue without undue discomfort to the subject, or heat damage to the adjacent tissue lining the body cavity receiving the applicator.

If, however, it is desired to heat the adjacent tissue lining the body cavity receiving the applicator, the cooling water would not be circulated through the cooling ducts 28. The described applicator may therefore be used for heating relatively remote tissue, in which case cooling water would be circulated through cooling ducts, or adjacent tissue, e.g., tissue, lining the cavity receiving the applicator, in which case there would be no circulation of cooling fluid through the cooling ducts.

The provision of the thermocouples 50a-50c adjacent to the outer face of the jacket but thermally insulated from the cooling ducts 28, and the provision of the balloon pressing the thermocouples against the body tissue, produce a more precise measurement of the temperature of the body tissue being heated by the applicator. Moreover, by passing the electrical conductors to the thermocouples axially along the outer face of reflector 52 (conductor sections 54a, FIG. 3) and then circumferentially (conductor sections 54b, FIG. 3) to their respective thermocouples 50a-50c, the measurements produced by the thermocouples are substantially insensitive to the heat and electromagnetic field produced by the microwave antenna, thereby further increasing the precision of the temperature measurements of the body tissue.

While the invention has been described with respect to a microwave heating applicator for insertion into the body rectum, it will be appreciated that the invention could be used in applicators for insertion into other body openings, or with other forms of devices for medical treatment or for medical diagnosis. For example, the jacket of the applicator could be first inserted into the opening, and then an imaging device, such as an x-ray or ultra-sonic imaging device, could be inserted into its bore 26 for imaging the interior of the body cavity. The imaging device could then be removed while leaving the jacket in place, and then a treating device, such as the above described microwave antenna or an ultrasonic treating device, could be inserted into bore 26 for rendering the medical treatment.

Many other variations, modifications and applications of the invention will be apparent.

What is claimed is:

1. An applicator for insertion into a body opening for medical treatment or for diagnostic purposes, characterized in that said applicator includes: an elongated jacket having a proximal open end and a distal closed end for insertion into the body opening; a disposable sleeve of elastomeric material also having a proximal open end and a closed distal end received on said jacket; and a balloon of elastomeric material integrally formed with and joined to said disposable sleeve at one side of said sleeve and jacket, said balloon occupying only the distal end of said disposable sleeve and being inflatable by a fluid to press the opposite side of the jacket and sleeve facing away from the balloon laterally against the tissue of the body opening, thereby to fix the position of the jacket within the body opening and to conform the pressed body tissue to the shape of said opposite side of the jacket and sleeve.

2. The applicator according to claim 1, wherein said balloon is of generally conical configuration when inflated, having a narrow tip at one end where joined to said sleeve and a wide base at the opposite end for engagement with the body tissue at said one side of the sleeve.

3. The applicator according to claim 1, further including a microwave antenna disposed within said jacket, said jacket further including cooling ducts adjacent its outer surface for circulating a cooling fluid therethrough in order to prevent undue heating of the body tissue in direct contact therewith, said balloon, when inflated, thereby also effecting efficient cooling of the body tissue in contact with said opposite side of the sleeve.

4. The applicator according to claim 3, wherein said jacket further includes a reflector at said one side for reflecting the microwave energy produced by said microwave antenna through said opposite side, and for concentrating the energy to a selected region of the body tissue at said opposite side of the sleeve.

5. The applicator according to claim 4, wherein said microwave antenna includes an inner electrical conductor, a layer of dielectric thereover, serving as a dielectric loading and an outer electrical conductor in the form of a braid having an the outer end folded back over itself at one end of the antenna and being dielectrically separated from the underlying electrical braid by another dielectric layer, thereby forming a dielectric loaded antenna in which the folded back portion of the electrical braid serves as an RF choke suppressing electromagnetic interference.

6. The applicator according to claim 4, wherein said jacket further includes a temperature measuring device adjacent to the outer surface of said opposite side of the sleeve, said balloon, when inflated, thereby also effecting efficient measurement of the temperature of the body tissue in contact with said opposite side of the sleeve.

7. The applicator according to claim 6, wherein said temperature measuring device includes an electrical conductor having a first section passing axially of the jacket and reflector along the face of the reflector opposite to that facing the microwave antenna so as to be substantially shielded therefrom by the reflector, and a second section passing circumferentially of the jacket from its first section shielded by the reflector to the temperature measuring device.

8. The applicator according to claim 6, wherein there are a plurality of said temperature measuring devices spaced axially of said jacket, each of said temperature measuring devices being a thermocouple attached to the outer face of the jacket and thermally insulated therefrom.

9. A disposable flexible sleeve of a size for receiving an applicator to be inserted into a body opening for medical treatment or for diagnostic purposes, characterized in that said sleeve is of an inflatable elastomeric material closed at one end and open at the opposite end, and has a balloon integrally formed with and joined to said sleeve at one side thereof, said balloon occupying only the closed end of said disposable sleeve, a tubelet extending externally of the sleeve and connected to said balloon to inflate the balloon and thereby to cause the balloon to press the opposite side of the sleeve and the corresponding side of the applicator, when received therein, laterally against the tissue of the body opening, thereby to fix the position of the applicator within the body opening and to conform the pressed body tissue to the shape of said opposite side of the sleeve and applicator therein.

10. The disposal sleeve according to claim 9, wherein said balloon is of generally conical configuration when inflated, having a narrow tip at one end where joined to said disposable sleeve and a wide base at the opposite end for engagement with the body tissue at said one side of the sleeve.

* * * * *